(12) United States Patent
McDonald et al.

(10) Patent No.: US 6,450,166 B1
(45) Date of Patent: Sep. 17, 2002

(54) PATIENT OXYGEN DELIVERY SYSTEM

(75) Inventors: Lee McDonald; Maurice Lavimodiere, both of Barrie (CA)

(73) Assignee: Southmedic Incorporated, Ontario (CA)

( * ) Notice: Subject to any disclaimer, the term of this patent is extended or adjusted under 35 U.S.C. 154(b) by 0 days.

(21) Appl. No.: 09/572,637

(22) Filed: May 17, 2000

(51) Int. Cl.[7] .............................................. A62B 18/08
(52) U.S. Cl. .............................. 128/206.27; 128/201.22
(58) Field of Search ....................... 128/200.24, 200.28, 128/202.18, 204.18, 205.25, 206.12, 206.26, 206.27, 207.11, 207.17, 206.28, 201.22

(56) References Cited

U.S. PATENT DOCUMENTS

| | | | |
|---|---|---|---|
| 1,974,828 A | | 9/1934 | Markut |
| 3,040,741 A | | 6/1962 | Carolan |
| 3,056,402 A | * | 10/1962 | Dickinson ................... 128/141 |
| 3,092,105 A | * | 6/1963 | Gabb .......................... 128/146 |
| 3,234,940 A | * | 2/1966 | Morton, Jr. ................. 128/146 |
| 3,347,229 A | * | 10/1967 | Heitman .................... 128/146.3 |
| 3,599,635 A | * | 8/1971 | Ansite ....................... 128/146.7 |
| 3,683,907 A | | 8/1972 | Cotabish |
| 3,850,168 A | | 11/1974 | Ferguson |
| 4,593,688 A | | 6/1986 | Payton |
| 4,739,757 A | | 4/1988 | Edwards |
| 5,575,282 A | | 11/1996 | Knoch |
| 5,653,228 A | * | 8/1997 | Byrd ...................... 128/207.11 |
| 5,697,363 A | * | 12/1997 | Hart ....................... 128/201.24 |
| D449,883 S | * | 10/2001 | McDonald et al. ........ D24/110 |

FOREIGN PATENT DOCUMENTS

| | | |
|---|---|---|
| CA | 1128826 | 8/1982 |
| CA | 2251531 | 10/1997 |
| WO | WO 97/38746 | 10/1997 |
| WO | WO 99/13929 | 3/1999 |

\* cited by examiner

*Primary Examiner*—John G. Weiss
*Assistant Examiner*—Teena Mitchell
(74) *Attorney, Agent, or Firm*—Nikolai & Mersereau, P.A.

(57) ABSTRACT

A lightweight oxygen delivery system for a patient comprising a curved resilient headband to extend from side to side over a patient's head and to be comfortably seatably engaged thereon. A clip is secured towards one end of the headband. An elongated tubular boom is secured at one end to the clip to extend and hold its position, when in operation from said one end at the clip to another end located at a space in front of, and proximal to the patient's nose and mouth. An oxygen diffuser port is located at the other end of the boom, to deliver oxygen from the boom to the space in the vicinity of the patient's nose and mouth. The clip is constructed so as to hold securely an oxygen delivery tube from an oxygen source in fluid communication with said one end of the boom so as to deliver oxygen from the source to the boom for discharge through the diffuser.

14 Claims, 5 Drawing Sheets

PATIENT OXYGEN DELIVERY SYSTEM

BACKGROUND OF THE INVENTION

The present invention relates to a novel system for delivery of oxygen to a patient, and more particularly relates to a device which can be used to replace conventional oxygen masks and nose cannula oxygen delivery systems.

Mask oxygen therapy has been around for a very long time and has seen virtually no changes. Problems encountered with this style of therapy are well known but unavoidable using the mask as it is supplied today. A number of vendors supply oxygen masks as a commodity item, with the result that there has been little or no improvement in the technology because of the low profit margins accompanying the sale of such masks.

Conventional oxygen masks comprise tent like structures which are strapped over the nose and mouth of a patient, often using an elastic band or bands behind the patient's ears or head. Oxygen is fed from a supply through a tube into the bottom portion of the mask at the front of the patient.

Common problems with the mask include:
1. Some patients find it claustrophobic.
2. Many patients cannot tolerate the smell of plastic resin.
3. Patients must take the mask off to speak or eat thereby discontinuing therapy.
4. Some patients are allergic to the elastic (latex allergy).
5. Some patients feel ill when they wear an oxygen mask, (the psychological effect is truly remarkable on the patient and the patient's family alike).
6. Patients often aspirate if they vomit while wearing the mask.
7. The mask cannot be used during facial surgery due to intrusion into the sterile field.
8. The mask cannot be worn if the patient has facial injuries such as burns.
9. Skin irritation is often found from the plastic.
10. The face mask does not effectively fit all sizes and shapes of face. Often the soft plastic masks are delivered in a deformed fashion.
11. The face mask usually necessitates clipping the oxygen delivery tube in front of the patient at the bottom of the mask. This is awkward and inconvenient as it may interfere with a patient's movement.
12. The face mask creates irregular infusion of oxygen by the patient, with exhaled air from the patient being mixed with oxygen in the mask.

Another current approach to oxygen delivery to a patient employs an oxygen delivery tube with tubular open ended nasal prongs or cannulae, at the delivery end of the tube, for insertion into a patient's nasal passages. Disadvantages of nasal cannulas include:
1. The patient may not be a nose breather.
2. Patients often get nose bleeds from the dryness of the nasal cannulas.
3. Patients find the front oxygen cord, necessary with nasal cannulas, difficult to handle as it hangs down directly in front of them and applies downward pressure on their ears, where the cord is again suspended, as in the case of masks.

Of background interest is U.S. Pat. No. 4,593,688 of Payton issued Jun. 10, 1986, which describes and illustrates a tubular system for, example, delivering nebulized oxygen enriched fog or the like to the face and mouth of a croup patient, the tube being suspended, at its delivery end, from a series of straps secured about a patient's head. A portion of the tube is mounted on a pivoting, unshaped frame member so that the tubing is held in front of and below the patient's face, for delivery of the nebulized oxygen enriched fog. The gas delivery to the nose and mouth area of the patient is through orifices in the tube, near the patient's nose and mouth when the tube is in position. This system is intended for children, and would be uncomfortable and restrictive to one's movements, if placed in position on a patient for a long period of time.

Also of background interest is PCT application WO 99/13929 published Mar. 25, 1999 of Combs et al. This reference describes and illustrates an oxygen delivery system for non-medical uses, for instance in oxygen bars or for oxygen enhancing during exercises such as aerobics or weight lifting. The system comprises a re-usable headset and a conduit to direct oxygen from a source to a headset and to a region proximate to the user's nose and mouth. The conduit is supported by a delivery arm which is preset to a predetermined distance from a user's head for proper supply of oxygen to the user's nose and mouth area.

Also relevant is Knoch et al U.S. Pat. No. 5,575,282 issued Nov. 19, 1996, which describes and illustrates a distribution system for oxygen to a patient's nose and mouth. This system includes a helix for mixing and spirally delivering oxygen towards the patient.

It is an object of the present invention to provide a lightweight system for delivery of oxygen to a patient, which avoids many of these problems of conventional masks and nasal cannulae, and which is suited for medical use.

SUMMARY OF THE INVENTION

In accordance with the present invention there is provided a lightweight oxygen delivery system for a patient comprising a curved resilient headband to extend from side to side over a patient's head and to be comfortably seatably engaged thereon. A clip is secured towards one end of the headband. An elongated tubular boom is secured at one end to the clip to extend and hold its position, when in operation from said one end at the clip to another end located at a space in front of, and proximal to the patient's nose and mouth. An oxygen diffuser port is located at the other end of the boom, to deliver oxygen from the boom to the space in the vicinity of the patient's nose and mouth. The clip is constructed so as to hold securely an oxygen delivery tube from an oxygen source in fluid communication with said one end of the boom so as to deliver oxygen from the source to the boom for discharge through the diffuser.

In an alternative embodiment of the present invention the boom further comprises a second tube for oxygen delivery, the other of which is designated for oxygen/carbon dioxide monitoring. This second tube is secured at one end to the clip and has at its other end an oxygen/carbon dioxide inlet port when in operation to be located at a space proximal to the patient's nose and mouth. The clip is constructed so as also to hold securely an oxygen/carbon dioxide monitor tube in fluid communication with the oxygen/carbon dioxide tube of the boom, for delivery of oxygen/carbon dioxide from the space in the vicinity of the patient's nose and mouth to an oxygen/carbon dioxide monitor.

The system of the present invention, as will be described in more detail subsequently, avoids many of the problems inherent with conventional medical oxygen delivery systems such as face masks and nasal cannulae.

BRIEF DESCRIPTION OF THE DRAWINGS

These and other advantages of the invention will become apparent upon reading the following detailed description and upon referring to the drawings in which.

Figure 1:
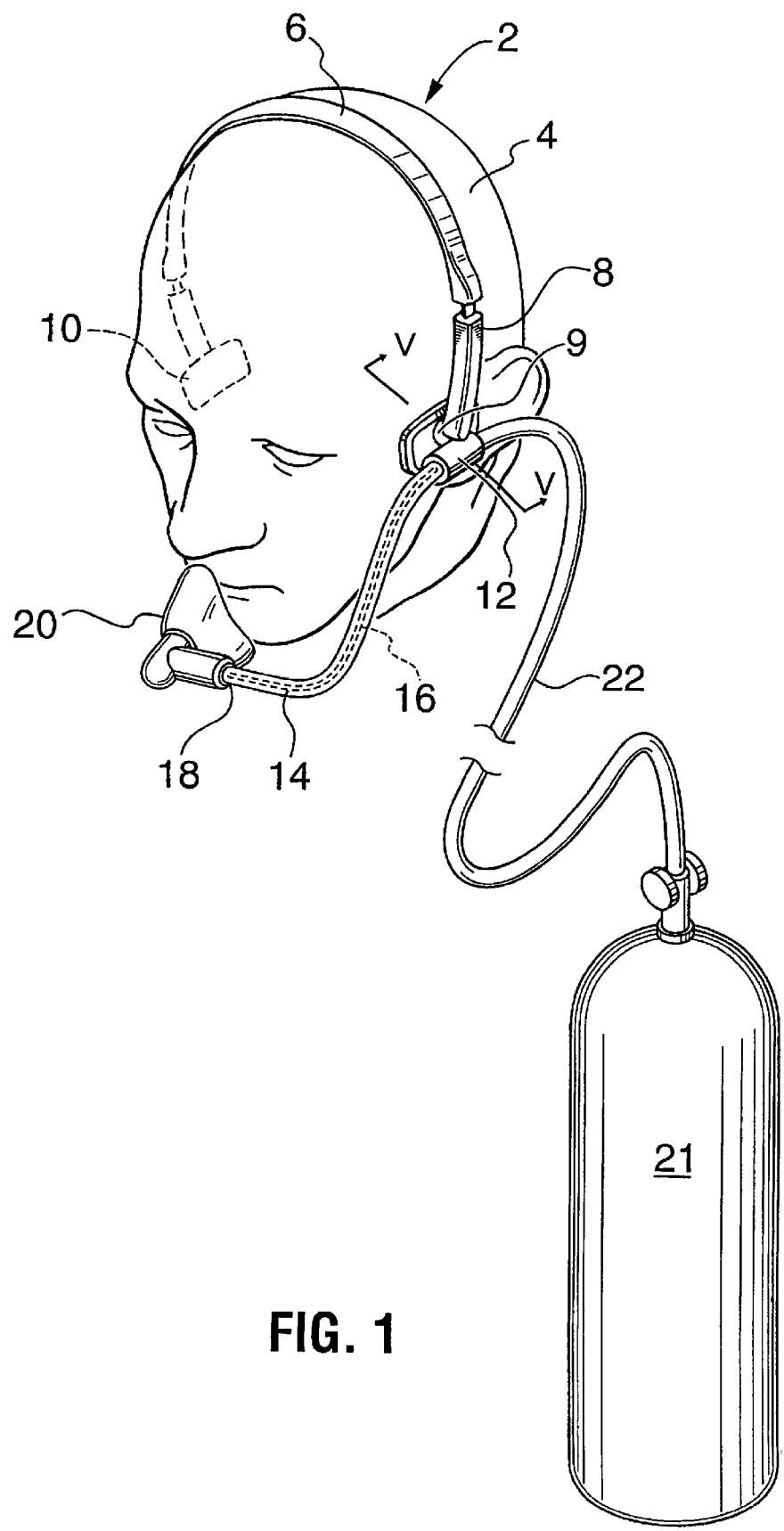
FIG. 1 is a perspective view of an oxygen delivery system according to the present invention mounted on the head of a patient.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE PREFERRED EMBODIMENTS

In the following description, similar features in the drawings have been given similar reference numerals.

Turning to FIG. 1, there is shown a lightweight delivery system 2, in accordance with the invention, mounted on the head 4 of a patient. The system comprises a curved resilient headband 6 which is provided with suitable adjustment means such as telescopic portions 8 and swivel connections 9, to enable the headband to be seated comfortably, from side to side over or behind the patient's head (or in positions therebetween). A pair of soft pads 10, made of rubber or other suitable material, are secured to swivel connections 9 and to the insides of the end portions of headband 6. To one side of headband 6 is secured a clip 12, which in the illustrated embodiment is of sleeve-like configuration. Secured to clip 12 is a tubular boom 14 which extends downwardly and forwardly to end, as illustrated, at a space in the vicinity of the patient's nose and mouth. Boom 14 is preferably a plastic tube in which is embedded a positioning wire 16 which enables the tube to be bent into an appropriate shape to position the lower end 18 of boom 14 appropriately for delivery of oxygen to the patient, and to be held in that position. At this lower end 18 of boom 14 is secured an oxygen diffuser 20 through which oxygen, fed into boom 14, is passed into the space in front of the patient's nose and mouth. The boom construction of the system according to the present invention enables adjustment from left to right and from front to back for precise oxygen delivery. The key is that the diffuser 20 preferably sits centrally approximately one half inch from the patient's mouth and nose. Diffuser 20 allows for the administration of the oxygen flow to the patient without the patient feeling a direct flow of air onto his/her face. From an appropriate oxygen source 21 an oxygen delivery tube 22 extends and is releasably engaged in the sleeve of clip 12 as illustrated for fluid communication with the tubular boom 14. In this manner clip 12 provides for oxygen delivery from tube 22 to boom 14 and diffuser 20.

Figure 2:
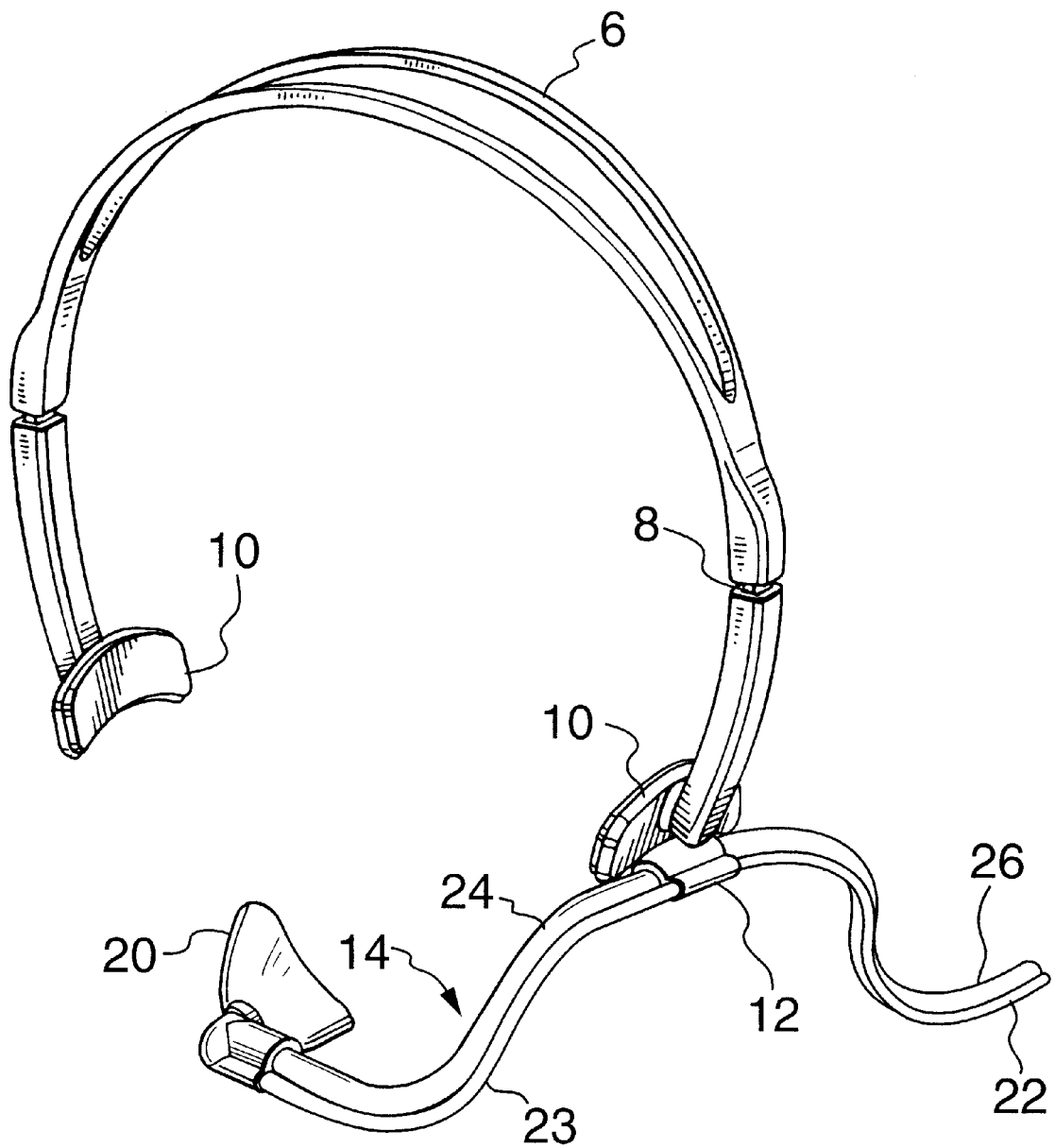
FIG. 2 is a perspective view of an alternative embodiment of oxygen delivery system according to the present invention.

In FIG. 2 there is illustrated a similar oxygen delivery system with the exception that tubular boom 14 incorporates a pair of tubes, one of which (23) is designed for oxygen delivery, the other of which (24) is intended to collect oxygen/carbon dioxide in the space of the vicinity of the patient's nose and mouth and deliver that sample to an oxygen/carbon dioxide monitor (not illustrated) through tube 26. Tube 26 is releasably secured, during operation, within clip 12, for fluid communication with the corresponding oxygen/carbon dioxide monitor tube 24 of boom 14. Preferably tubes 23 and 24 are of integral construction. An appropriate oxygen/carbon dioxide inlet port 28 (FIG. 4) is associated with diffuser 20, as will be described in more detail subsequently.

The oxygen delivery system according to FIGS. 1 and 2 is comfortable and adjustable for all head sizes. The use of the thin side cushions allows a patient to lie on his/her side with comfort.

Figure 3:
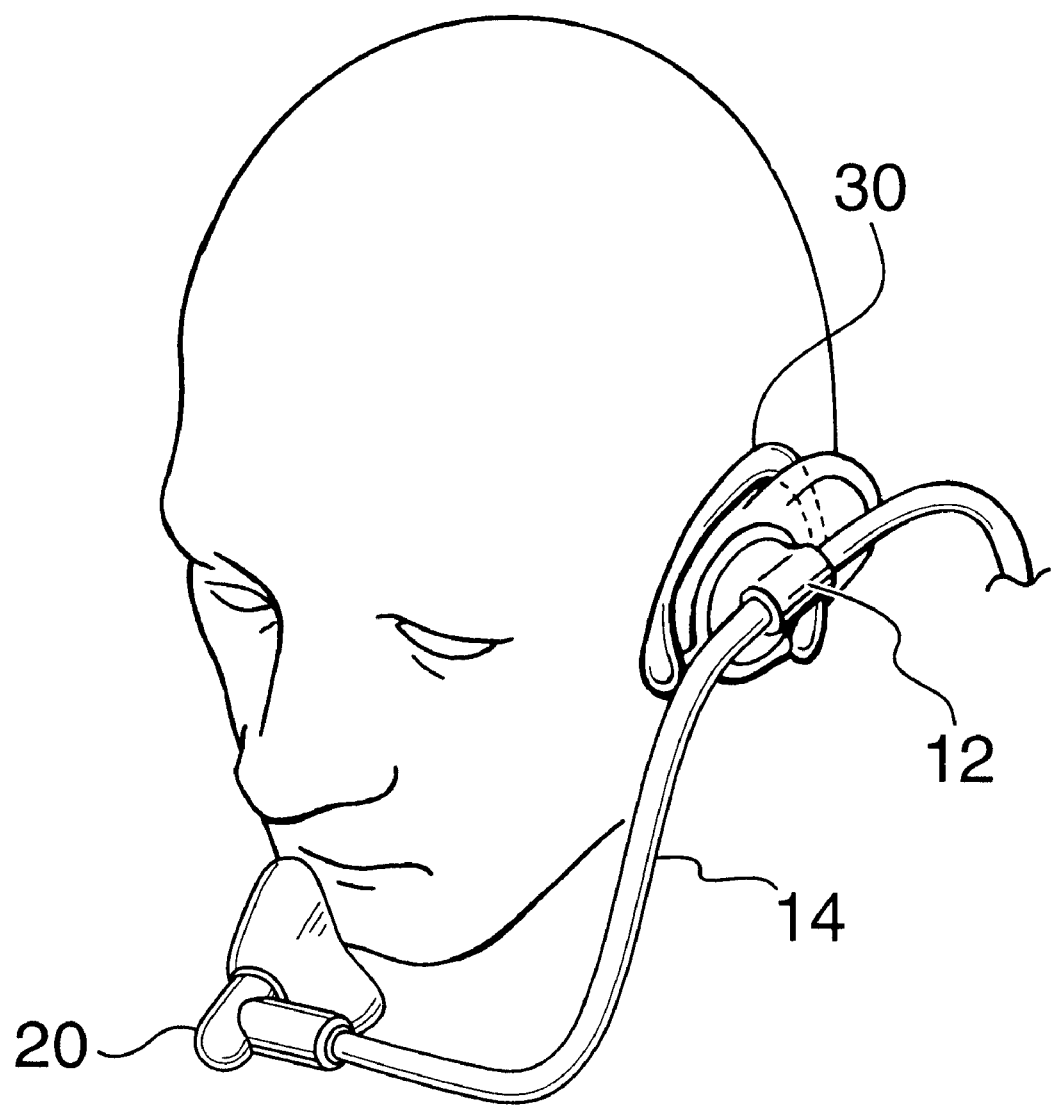
FIG. 3 is a perspective view of yet a further alternative embodiment of oxygen delivery system according to the present invention.

While the device of FIGS. 1 and 2 is shown with a headband, optional means of securing boom 14 in position for oxygen delivery to a patient by means of a conventional over-the-ear mount 30 is shown in FIG. 3. Other conventional securing means may also be appropriate.

Figure 4:
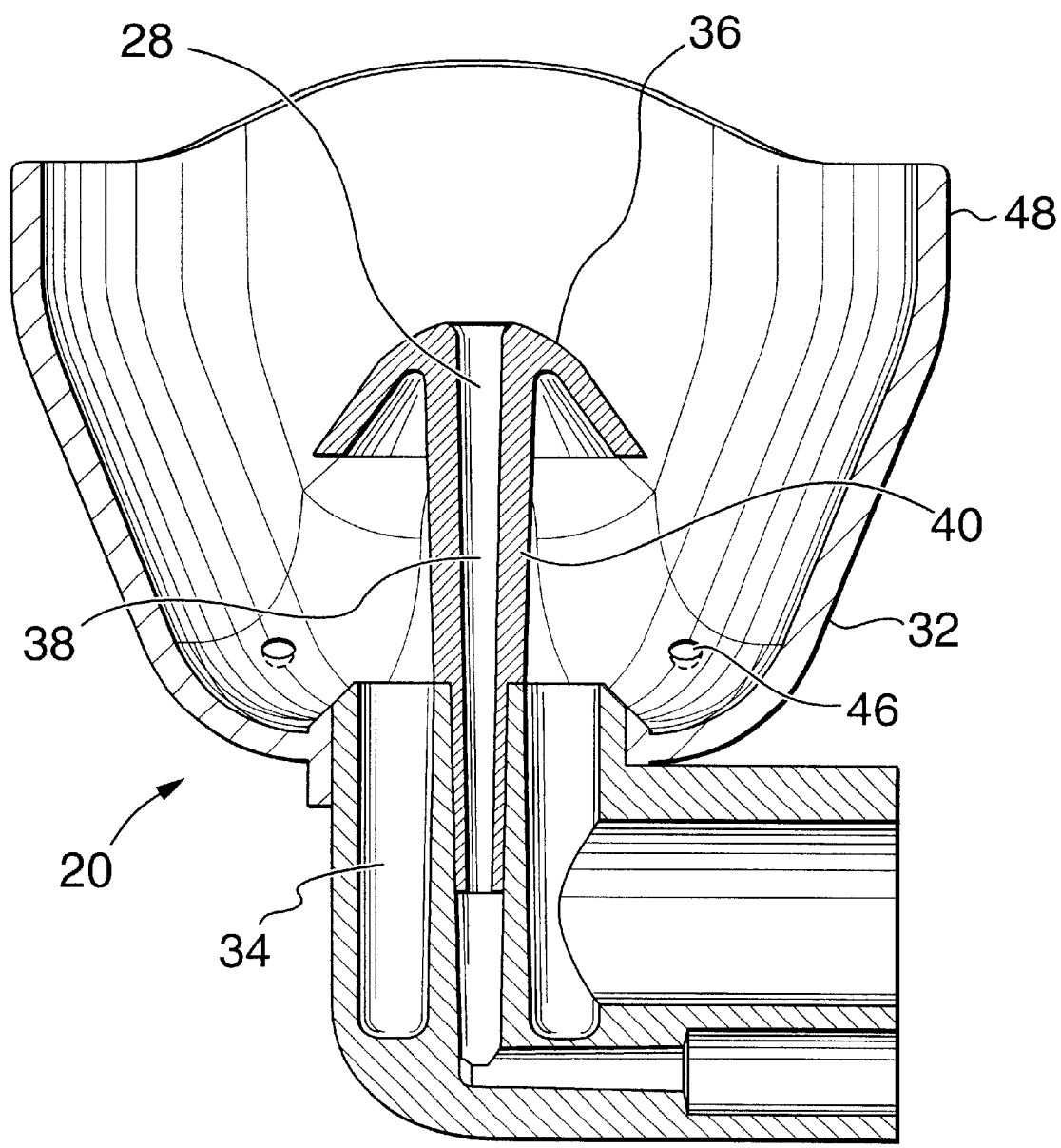
FIG. 4 is a section view of the diffuser port of the devices of FIGS. 1, 2 and 3.

A preferred form of diffuser 20 is detailed in partial section in FIG. 4. Its body 32, having an interior surface of generally concave configuration, circumscribes the oxygen outlet end of oxygen delivery tube 23 and directs the flow of oxygen generally towards the patient's mouth and nose when the diffuser 20 is properly positioned and operational. A mushroom-shaped baffle 36 is seated over oxygen outlet 34 so as to assist in the diffusion of oxygen and avoid a direct flow of oxygen towards the patient's face. Baffle 36 impedes oxygen flow from the rear of the body 32, inducing a transmission from jet to turbulent flow. Details of the shape of the baffle 36 and body 32 directly influence the mixing characteristics between pure oxygen stream and the ambient air (containing approximately 21% oxygen by volume), and thus determine the oxygen content of the plume delivered from the diffuser to the surface of the patient's face. As illustrated, the baffle 36 may have a passageway 38 to permit gas analysis of expired gases, passageway 38 constituting a sampling port which is bored on center and axially through the stem 40 of baffle 36.

As well, body 32 of diffuser 20 has a contoured inner surface, forming a cup shape which follows the shape of the nose/mouth nexus of a patient, thereby forming a shaped plume that directs the oxygen stream towards the patient's face. The enclosed volume of that cup may be modified to accommodate a larger plume and increase the total oxygen delivered during respiratory inspiration. As can be seen in FIG. 4, the rim 48 of body 32 becomes more cylindrical (with opposite sides being parallel) than outwardly extending, as are the lower portions of the body. This shaping of the rim edges of the body permits a concentrating of oxygen and a shaping of the plume, providing a more precise direction of the plume of oxygen towards the patient's nose/mouth.

Of course the overall shaping of body 32 and baffle 36 may be modified to suit the requirements of a particular application or user need.

Where the delivery system incorporates an oxygen/carbon dioxide monitoring function, a passage way 38 through the stem 40 of baffle 36 communicates directly with oxygen/carbon dioxide monitor tube 24, thereby enabling a sample of oxygen or carbon dioxide, in the region of the patient's mouth and nose, to be drawn to the oxygen/carbon dioxide monitor (situated at a remote location)

Figure 5:
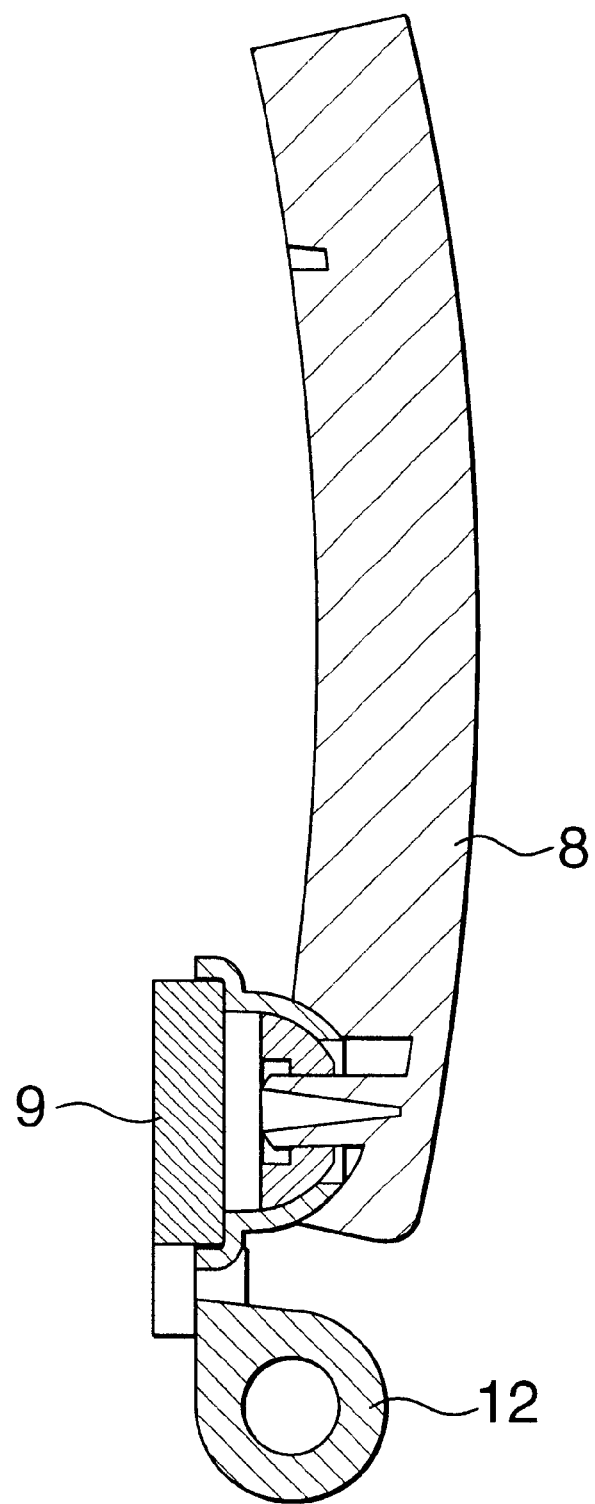
FIG. 5 is a section view along line V—V of FIG. 1, showing in detail an embodiment of pivoting attachment of headband and clip in accordance with the present invention.

The adjustability and versatility of the headband version of delivery oxygen delivery system in accordance with the present invention, as illustrated in FIGS. 1 and 2, is enhanced by the semi-universal swivel connection 9 detailed in FIG. 5. This swivel enables the headband to be swivelled rearwardly to be seated behind a patient's head or in intermediate positions, with soft pads 10 maintaining their seated engagement on either side of the patient's head.

It is also envisaged that a ridge or plurality of scented material holding pockets 42, in the surface of the diffuser body 32 may be provide for purposes of aroma therapy a layer of scented material may be coated on the back of the diffuser.

Advantages of the present system, for delivery of oxygen to a patient, over prior art devices, include:

eliminating the possibility of the patient aspirating should they be ill during oxygen therapy, lightweight, does not give the patient the feeling of being sick, rather has a high tech look that is positive for the patient, allows for the sampling and monitoring of expired carbon dioxide directly at the boom end, oxygen tubing comes off at the side instead of directly at the bottom of the mask as seen in traditional devices, oxygen tubing can be clipped to the patient's gown instead of adding to the weight of the delivery system on the patient's head, the device does not outgas as often happens with full face masks, no smell of plastic, no need to remove oxygen therapy while patient is eating or speaking, well tolerated by patients; provides comfort not found with traditional devices, could be reused for a longer period of time than conventional masks and nose cannula systems, allows for the administration humidified air as well as non-humidified air, one size adjusts for a wide range of patent sizes, effective whether the patient is a mouth or nose breather, permits adjusting to be clear of any particular area on a patent's head.

The oxygen delivery system of the present invention is envisaged as having particular application where a patient has his/her faculties and is not in a state where the head strap or ear mount might be unintentionally dislodged, or the diffuser and associated boom might be unintentionally displaced from normal, operative position.

The oxygen delivery system of the present invention can be used not only for oxygen therapy for a patient in a hospital bed, but also in sports therapy clinics or for the administration of oxygen to athletes, for oxygen therapy to patients who have had facial surgery and cannot tolerate a mask, in sleep therapy clinics, for outpatient and home oxygen therapy and even for oxygen delivery to a patient in an operating room during surgery.

As for children, this population traditionally does not tolerate mask oxygen therapy. The device according to the present invention is not only likely to be considered to be stylish, by older children, it could support decorations to represent popular cartoon characters, or the like, to appeal to younger children.

Thus, it is apparent that there has been provided in accordance with the invention a lightweight oxygen delivery system that fully satisfies the objects, aims and advantages set forth above. While the invention has been described in conjunction with illustrated embodiments thereof, it is evident that many alternatives, modifications and variations will be apparent to those skilled in the art in light of the foregoing description. For example, a multi lumena boom 14, instead of one having a single or a pair of tubes, may be provided, each tube having a distinct function. Accordingly, it is intended to embrace all such alternatives, modifications and variations as fall within the spirit and broad scope of the invention.

What is claimed is:

1. A lightweight oxygen delivery system for a patient comprising:
   (a) a curved resilient headband having first and second ends and adapted to extend from side to side over a patient's head and to be comfortably seatably engaged thereon;
   (b) a clip secured towards one end of the headband;
   (c) an elongated tubular boom secured at one end thereof to the clip and constructed to extend and hold a position, when in operation, with another end located at a space in front of, and proximal to the patient's nose and mouth;
   (d) an oxygen diffuser with a an oxygen outlet at said other end of the boom, to deliver oxygen from the boom to a space in the vicinity of the patient's nose and mouth the diffuser comprising a body having an interior surface of generally concave configuration, to direct a plume of oxygen-enriched air generally towards the patient's mouth and nose through the oxygen outlet, and a baffle seated over the oxygen outlet so as to assist in mixing of oxygen with ambient air and avoid a direct flow of oxygen towards the patient's face;

the clip constructed so as to hold securely an oxygen delivery tube from an oxygen source in fluid communication with said one end of the boom so as to deliver oxygen from the source to the boom for discharge through the diffuser port.

2. A system according to claim 1 wherein an internal side of the first and second ends of the headband are provided with a cushion means.

3. A system according to claim 2 wherein the headband is provided with means to adjust the size of the band for comfortable seating on a patient's head.

4. A system according to claim 1 wherein a wire is embedded in the tubular boom to permit bending of the boom to a particular shape and maintaining of that shape.

5. A system according to claim 1 wherein the clip comprises a hollow sleeve constructed so as to releasably receive in frictional engagement the oxygen tube from the oxygen source.

6. An oxygen delivery system according to claim 1 wherein pivotally secured to the clip.

7. A system according to claim 1 wherein the boom further comprises a second tube designated for oxygen/carbon dioxide monitoring, this second tube being secured at one end to the clip and having at its other end an oxygen/carbon dioxide inlet port when in operation to be located within the diffuser body at a space proximal to the patient's nose and mouth and wherein the clip is constructed so as to also hold securely an oxygen/carbon dioxide monitor tube in fluid communication with the oxygen/carbon dioxide tube of the boom and adapted for delivery of oxygen/carbon dioxide from the corresponding space in the vicinity of the patient's nose and mouth to an oxygen/carbon dioxide monitor.

8. A system according to claim 7 wherein the oxygen/carbon dioxide monitoring tube is an integrally combined part of the boom.

9. A system according to claim 7 wherein the diffuser comprises a body having an interior surface of generally concave configuration to direct the flow of oxygen generally towards the patient's mouth and nose.

10. A system according to claim 9 wherein the diffuser further comprises a baffle seated over the oxygen outlet so as to assist in the mixing with ambient air of oxygen and avoid a direct flow of oxygen towards the patient's face.

11. A system according to claim 10 wherein a passageway through the baffle communicates directly with oxygen/carbon dioxide monitor tube thereby enabling a sample of oxygen or carbon dioxide, in the region of the patient's mouth and nose, to be drawn to the oxygen/carbon dioxide monitor.

12. A system according to claim 11 further comprising a source of scented material in the diffuser, for purposes of aroma therapy.

13. A system according to claim 1 wherein an internal side of each of the first and second ends of the headband is provided with a cushion means wherein the headband is pivotably secured to the cushion means and clip so as to be positionable across the top of or behind the patient's head.

14. A lightweight oxygen delivery system for a patient comprising:
(a) an over the ear mount in use to be comfortably seatably engaged on a patient's ear;
(b) a clip secured to the mount;
(c) an elongated tubular boom secured at one end to the clip and constructed to extend and hold a position, when the mount is in position on a patient's ear, with another end located at a space in front of and proximal to the patient's nose and mouth;
(d) an oxygen diffuser at said other end of the boom, to delivery oxygen from the boom to a space in the vicinity of the patient's nose and mouth the diffuser comprising a body having an interior surface of generally concave configuration, to direct a plume of oxygen-enriched air generally towards the patient's mouth and nose through the oxygen outlet, and a baffle seated over the oxygen outlet so as to assist in mixing of oxygen with ambient air and avoid a direct flow of oxygen towards the patient's face;

the mount being constructed so as to support the boom and diffuser in position with respect to the patient's nose and mouth, the clip constructed so as to hold securely an oxygen delivery tube from an oxygen source in fluid communication with said one end of the boom so as to deliver oxygen from the source to the boom for discharge through the diffuser.

* * * * *